(12) United States Patent
Masson et al.

(10) Patent No.: US 9,733,217 B2
(45) Date of Patent: Aug. 15, 2017

(54) METHOD AND APPARATUS FOR PROVIDING A STRUCTURAL CONDITION OF A STRUCTURE

(75) Inventors: Patrice Masson, Sherbrooke (CA);
Philippe Micheau, Sherbrooke (CA);
Nicolas Quaegebeur, Sherbrooke (CA);
Dominique Langlois Demers, Waterloo (CA)

(73) Assignee: Scopra Sciences et Génie s.e.c., Sherbrooke, Québec ( * ) Notice: Subject to any disclaimer, the term of this patent is extended or adjusted under 35 U.S.C. 154(b) by 671 days.

(21) Appl. No.: 13/582,822

(22) PCT Filed: Mar. 4, 2011

(86) PCT No.: PCT/CA2011/000254
§ 371 (c)(1),
(2), (4) Date: Nov. 16, 2012

(87) PCT Pub. No.: WO2011/106890
PCT Pub. Date: Sep. 9, 2011

(65) Prior Publication Data
US 2013/0055816 A1    Mar. 7, 2013

Related U.S. Application Data

(60) Provisional application No. 61/310,996, filed on Mar. 5, 2010.

(51) Int. Cl.
*G01N 29/07*    (2006.01)
*G01N 29/06*    (2006.01)
(Continued)

(52) U.S. Cl.
CPC ........... *G01N 29/069* (2013.01); *G01N 29/07* (2013.01); *G01N 29/226* (2013.01);
(Continued)

(58) Field of Classification Search
CPC ....... G01N 29/04; G01N 29/12; G01N 29/045
(Continued)

(56) References Cited

U.S. PATENT DOCUMENTS 4,545,251 A    10/1985    Uchida et al.
5,996,413 A *  12/1999    Iyer et al. .................. 73/592
(Continued)

FOREIGN PATENT DOCUMENTS

CA    2360759    5/2001
CA    2679293    9/2008
(Continued)

OTHER PUBLICATIONS

International Search Report for International Application No. PCT/CA2011/000254 dated Jun. 23, 2011.

*Primary Examiner* — Paul West
*Assistant Examiner* — Mark A Shabman
(74) *Attorney, Agent, or Firm* — Fasken Martineau DuMoulin

(57) ABSTRACT

The invention relates to a method for providing a structural condition of a structure, comprising providing an excitation wave generator; providing an excitation wave sensor; injecting an excitation burst wave into the structure using the excitation wave generator; obtaining a measured propagated excitation burst wave using the excitation wave sensor; correlating the measured propagated excitation burst wave with one of a plurality of theoretical dispersed versions of the excitation burst wave; and providing an indication of the structural condition of the structure corresponding to the correlated measured propagated excitation burst wave. The method may offer a better localization of the reflection points and thus of the potential defects present in a structure under inspection, when compared with a group velocity-based or time-of-flight (ToF) approach. The method may be
(Continued)

particularly useful for structural health monitoring (SHM) and Non-Destructive Testing (NDT). The method may also enable determination of the mechanical properties of the structure.

9 Claims, 12 Drawing Sheets

(51) Int. Cl.
  *G01N 29/22* (2006.01)
  *G01N 29/24* (2006.01)
  *G01N 29/34* (2006.01)
  *G01N 29/30* (2006.01)
  *G01N 29/44* (2006.01)

(52) U.S. Cl.
  CPC ......... *G01N 29/2475* (2013.01); *G01N 29/30* (2013.01); *G01N 29/343* (2013.01); *G01N 29/4427* (2013.01); *G01N 2291/0256* (2013.01); *G01N 2291/0258* (2013.01); *G01N 2291/044* (2013.01); *G01N 2291/101* (2013.01); *G01N 2291/102* (2013.01)

(58) Field of Classification Search
  USPC .......................................................... 73/579
  See application file for complete search history.

(56) References Cited

U.S. PATENT DOCUMENTS

| | | | | |
|---|---|---|---|---|
| 6,301,967 | B1* | 10/2001 | Donskoy et al. | 73/579 |
| 7,551,058 | B1* | 6/2009 | Johnson et al. | 340/10.41 |
| 2004/0231423 | A1 | 11/2004 | Dittrich et al. | |
| 2007/0150213 | A1 | 6/2007 | Kim et al. | |

FOREIGN PATENT DOCUMENTS

| | | |
|---|---|---|
| JP | 60256052 | 12/1985 |
| WO | WO 99/39194 | 8/1999 |

* cited by examiner

Table 1 Properties of the aluminium plate and piezoelectric array used for the simulation and the experimental validation.

| Component | Property | Value |
|---|---|---|
| Plate | Length | 0.71 m |
| | Width | 0.45 m |
| | Thickness | 0.0015 m |
| | Location of the hole | (0,0) m |
| | Diameter of the hole | 0.007 m |
| | Young's modulus | 67 GPa |
| | Shear modulus | 28 GPa |
| | Density | 2700 kg/m$^3$ |
| | Poisson's ratio | 0.33 |
| Array | Location of the array (center) | (-0.0966,-0.0594) m |
| | Number of circular elements | 7 |
| | Diameter of elements | 0.003 m |
| | Spacing between elements (center to center) | 0.003 m |
| | Thickness of the elements | 0.00025 m |
| | Piezoelectric type | PZT-5A (Piezo Systems, Inc.) |

FIGURE 2B

(a) EUSR using $c_g$.

(b) Excitelet approach.

(a) Mode $A_0$.

(b) Mode $S_0$.

(a) Mode $A_0$.

(b) Mode $S_0$.

(a) Mode $A_0$.

(b) Mode $S_0$.

(c) Modes $A_0$ and $S_0$.

METHOD AND APPARATUS FOR PROVIDING A STRUCTURAL CONDITION OF A STRUCTURE

CROSS-REFERENCE TO RELATED APPLICATIONS

This application is a National Phase Application of PCT International Application No. PCT/CA2011/000254, International Filing Date Mar. 4, 2011, which claims priority of US Provisional Patent application No. 61/310,996 filed on Mar. 5, 2010 and entitled "METHOD FOR IMAGING A STRUCTURAL CONDITION OF A STRUCTURE", the specification of which is hereby incorporated by reference.

FIELD OF THE INVENTION

The invention generally relates to imaging techniques and more particularly relates to a method and an apparatus for imaging a structural condition of a structure. It also relates to applications of the method for Structural Health Monitoring (SHM) and Non-Destructive Testing (NDT).

BACKGROUND OF THE INVENTION

Different imaging techniques have been developed for monitoring and control purposes.

For example, because of their extended area inspection and their small wavelength, which better interacts with small defects, Structural Health Monitoring (SHM) techniques based on guided wave propagation in structures have been used for many years.

The reflection of guided waves with defects in composite and metallic structures may be used for localizing such defects.

Mode conversion at defects has been exploited in detection strategies, either for simple structures using $A_0$ and $S_0$ Lamb waves, or in plate overlaps using incident $A_0$ and $S_0$ Lamb waves, and shear horizontal (SH) waves.

Efficient sensing and actuating schemes for SHM have been demonstrated using multiple piezoelectric elements. For example, approaches for embedded damage detection using pitch-catch configurations where piezoelectric elements are used on both sides of a suspected damage area for simple and complex structures have been disclosed. The representation of the energy carried by a propagating wave has been used in many approaches to identify reflection and transmission at discontinuities.

In order to minimize the footprint of sensors required for embedded damage detection, compact sensing strategies have been disclosed for pulse-echo configurations, with various array configurations.

Most of the damage detection and localization approaches are currently based on the measurement of a time-of-flight (ToF) and the knowledge of the group velocity for a mode propagating at a given frequency. Such approaches have been used within imaging techniques to process the signals measured by the elements of arrays.

As an example, the Embedded Ultrasonic Structural Radar (EUSR) uses a phased-array approach with a round-robin procedure to image defects located, in its simplest implementation, in the far-field of the array. In these approaches, the localization of the reflectors in the image relies on the maximum of the envelope of the measured burst.

For non-dispersive propagation, an accurate localization can be obtained. However, even if specific low-dispersive modes are injected and/or measured in the structure using selective actuators and sensors, mode conversion at discontinuities might generate dispersive modes which may superimpose with the targeted modes and significantly complicate the measurement of the ToF associated with the echoes in the time domain signal and therefore impair the localization of the reflectors and lead to biased diagnostic.

A number of approaches have been proposed to extract mode-related information from a time domain signal. The matching pursuit approach has been proposed to decompose time domain signals using Gabor time-frequency atoms. The approach has been improved using Gaussian chirps, trying to mimic the excitation signal used for detection, or using shifted and scaled versions of the excitation signal.

The analysis of dispersion using time-frequency tools has also attracted much attention, with new transforms such as chirplet transform and more recently, the warpogram. A number of researchers have proposed ways to compensate for the effect of the dispersion so that the shape of the input signal can be recovered in the measured signal, and thus a better estimate of the ToF may be provided. The comparison of various approaches has shown that dispersion compensation provides the least error on the estimate of the ToF.

However, these techniques are often quite complicated to implement and may lead to approximate localization of the defects present in the structure under inspection, which is a great disadvantage.

It would therefore be desirable to provide an improved method for imaging a structural condition of a structure that would reduce at least one of the above-mentioned drawbacks.

BRIEF SUMMARY

Accordingly, there is provided a method for providing a structural condition of a structure, comprising providing an excitation wave generator; providing an excitation wave sensor; injecting an excitation burst wave into the structure using the excitation wave generator; obtaining a measured propagated excitation burst wave using the excitation wave sensor; correlating the measured propagated excitation burst wave with one of a plurality of theoretical dispersed versions of the excitation burst wave; and providing an indication of the structural condition of the structure corresponding to the correlated measured propagated excitation burst wave.

The method may offer a better localization of the reflection points and thus of the potential defects present in a structure under inspection, when compared with a group velocity-based or time-of-flight (ToF) approach, which is of great advantage.

Moreover the method may be implemented in frequencies and modes ranges with high dispersion characteristics, which is of great advantage.

Since the method is based on the time-domain correlation of signals, i.e. scalar product of time domain signals, interference patterns are limited. This may enable to image damage sizes below generated wavelengths, which is also of great advantage.

Furthermore, in one embodiment, for a given application wherein the modes and frequencies are imposed by the kind of damage to detect, for instance for their through-the-thickness strain distribution or propagation characteristics, the method may offer an increased flexibility, which is also of great advantage.

In one embodiment, the providing of an excitation wave generator comprises embedding the excitation wave generator into the structure. The providing of an excitation wave sensor comprises embedding the excitation wave sensor into the structure. This is of great advantage since it may enable an embedded monitoring of the structure.

In another embodiment, the excitation wave generator and the excitation wave sensor are embedded in a handheld device removably mountable with the structure. This is of great advantage since it may enable Non-Destructive Testing (NDT).

In one embodiment, the injecting of an excitation burst wave into the structure and the obtaining of a measured propagated excitation burst wave are performed according to a pulse-echo configuration.

In another embodiment, the injecting of an excitation burst wave into the structure and the obtaining of a measured propagated excitation burst wave are performed according to a pitch and catch configuration.

In one embodiment, the method further comprises computing the plurality of theoretical dispersed versions of the excitation burst wave based on a theoretical representation of the structure before the correlating of the measured propagated excitation burst wave with one of a plurality of theoretical dispersed versions of the excitation burst wave. In a further embodiment, this plurality of theoretical dispersed versions of the excitation burst wave may be stored in a database.

In another embodiment, the method further comprises, before the injecting of an excitation burst wave into the structure: providing a reference structure; injecting the excitation burst wave into the reference structure using the excitation wave generator; obtaining a reference measured propagated excitation burst wave using the excitation wave sensor; and computing the plurality of theoretical dispersed versions of the excitation burst wave based on the reference measured propagated excitation burst wave. In a further embodiment, this plurality of theoretical dispersed versions of the excitation burst wave may be stored in a database.

In one embodiment, the indication of the structural condition of the structure comprises an image of the structure.

In another embodiment, the indication of the structural condition of the structure comprises an image comprising structural differences between the structure and the reference structure. In a further embodiment, the indication may be information related to whether the structure comprises at least one defect or not.

In still a further embodiment, the method comprises determining a structural property of the structure. In one embodiment, the structural property of the structure comprises a phase velocity of the structure.

In one embodiment, the excitation burst wave comprises a high frequency burst wave. In a further embodiment, the high frequency burst wave ranges from 100 kHz to 2 MHz.

In one embodiment, the correlating of the measured propagated excitation burst wave with one of a plurality of theoretical dispersed versions of the excitation burst wave comprises applying a chirplet-based matching pursuit technique.

In another embodiment, the excitation wave generator and the excitation wave sensor are embedded in a transducer having an array of elements, the injecting of an excitation burst wave into the structure and the obtaining of a measured propagated excitation burst wave being performed according to a round-robin technique.

In another embodiment, the correlating of the measured propagated excitation burst wave with one of a plurality of theoretical dispersed versions of the excitation burst wave is performed according to a multiple mode correlation.

In one embodiment, the structure is selected from a group consisting of a metallic structure and a composite structure.

According to another aspect, there is also provided the use of the method for providing a structural condition of a structure as previously defined for providing a localization and a dimension of a potential structural defect in the structure.

According to another aspect, there is also provided the use of the method for providing a structural condition of a structure as previously defined for Structural Health Monitoring (SHM).

According to another aspect, there is also provided the use of the method for providing a structural condition of a structure as previously defined for Non-Destructive Testing (NDT).

According to another aspect, there is also provided an apparatus for providing a structural condition of a structure. The apparatus comprises an excitation wave generator operatively mountable with the structure for injecting an excitation burst wave into the structure and an excitation wave sensor operatively mountable with the structure for obtaining a measured propagated excitation burst wave. The apparatus comprises a control unit operatively connected to the excitation wave generator and to the excitation wave sensor, the control unit being further operatively connectable to a database comprising a plurality of theoretical dispersed versions of the excitation burst wave. The control unit comprises a processing unit adapted for correlating the measured propagated excitation burst wave with one of the plurality of theoretical dispersed versions of the excitation burst wave to provide correlated measured data. The apparatus comprises a structural condition providing unit operatively connected to the control unit for providing an indication of the structural condition of the structure corresponding to the correlated measured data.

In one embodiment, each of the excitation wave generator and the excitation wave sensor is embedded in the structure.

In another embodiment, the excitation wave generator and the excitation wave sensor are embedded in a handheld device removably mountable with the structure.

In one embodiment, the excitation wave generator and the excitation wave sensor are embedded in a single transducer adapted for injecting the excitation burst wave into the structure and obtaining the measured propagated excitation burst wave.

In one embodiment, piezoceramic elements are used for generating the excitation wave and sensing the same once propagated in the structure.

In a further embodiment, the transducer comprises an array of elements operable according to a round-robin technique.

In one embodiment, the excitation wave generator and the excitation wave sensor are combined in a sparse array of transducers.

In one embodiment, the providing unit comprises a display unit.

In one embodiment, the indication of the structural condition of the structure comprises an image of the structure.

In another embodiment, the apparatus is adapted for determining a structural property of the structure. In a further embodiment, the structural property of the structure comprises a phase velocity of the structure.

According to another aspect, there is also provided the use of the apparatus for providing a structural condition of a structure as previously defined for providing a localization and a dimension of a potential structural defect in the structure.

According to another aspect, there is also provided the use of the apparatus for providing a structural condition of a structure as previously defined for Structural Health Monitoring (SHM).

According to another aspect, there is also provided the use of the apparatus for providing a structural condition of a structure as previously defined for Non-Destructive Testing (NDT).

These and other objects, advantages and features of the present invention will become more apparent to those skilled in the art upon reading the details of the invention more fully set forth below.

BRIEF DESCRIPTION OF THE DRAWINGS

In order that the invention may be readily understood, embodiments of the invention are illustrated by way of example in the accompanying drawings.

FIG. 2B is a table showing the properties of a plate and a transducer array used for an experiment, according to one embodiment of the invention.

Further details of the invention and its advantages will be apparent from the detailed description included below.

DETAILED DESCRIPTION

In the following description of the embodiments, references to the accompanying drawings are by way of illustration of examples by which the invention may be practiced. It will be understood that various other embodiments may be made and used without departing from the scope of the invention disclosed.

Throughout the present description, the implementation of a method for providing an indication of a structural condition of a structure such as whether or not the structure presents defects will be described. Such method may be particularly useful for Structural Health Monitoring (SHM), as it will become apparent to the skilled addressee, but it should nevertheless be appreciated that the method is not limited to such application and that various other particular applications may be considered. For example, the method may also be of particular interest for Non-Destructive Testing (NDT). In such a case, the method may be implemented with a handheld apparatus, as it will be detailed below.

In one embodiment, the structure under analysis comprises a metallic structure. In another embodiment, the structure under analysis comprises a composite structure. The skilled addressee will nevertheless appreciate that other types of structure may be considered for a given application.

The general principle of correlation approaches for analysis of dispersed signals is based on the use of elementary time-function, called atom functions, that are subject to mathematical operations, such as time-frequency shifts, in order to create a dictionary of functions that may then be correlated with an analyzed signal. The feature extraction may then be performed by minimizing the difference between synthesized and analyzed signals.

As it will become apparent below to the skilled addressee, the method for providing an indication of a structural condition of a structure uses a similar approach for imaging of reflectors in a structure. As it will be detailed thereinafter, in one embodiment, the structure may be mounted with compact and sparse piezoceramic arrays.

In one embodiment, the method uses a chirplet-based matching pursuit technique called excitelet for imaging, as it will become apparent to the skilled addressee upon reading of the present description. It is worth mentioning that the expression "matching pursuit technique" should be understood as encompassing any numerical technique which involves finding the best matching projections of multidimensional data onto an over-complete dictionary.

Figure 2A:
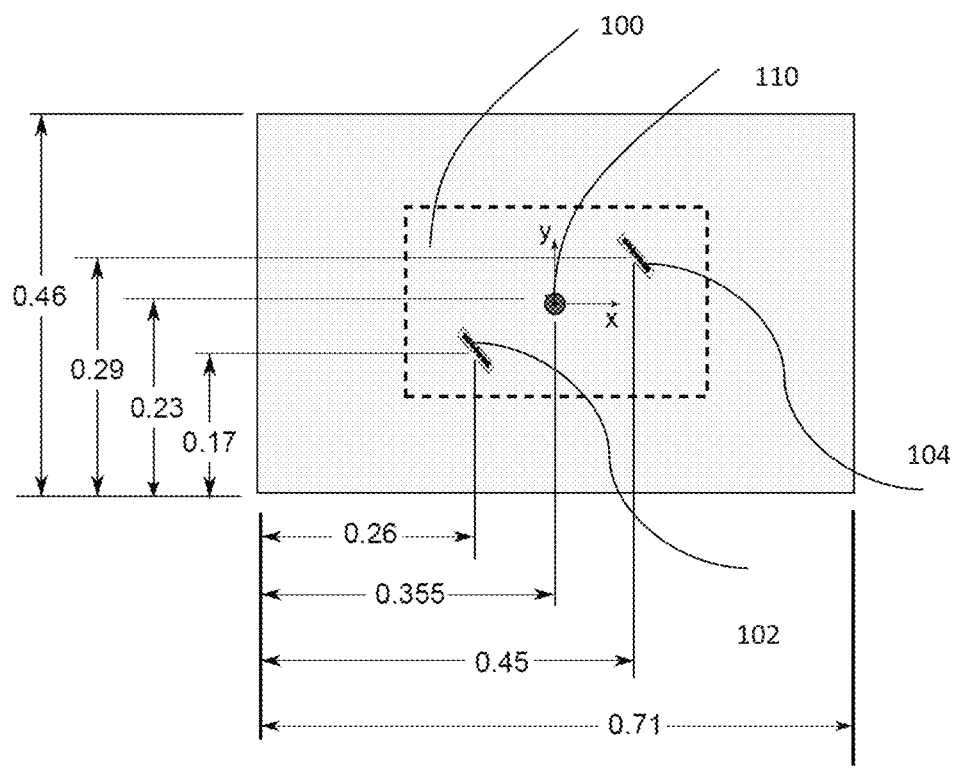
FIG. 2A shows a plate and the relative localization of two transducer arrays, according to one embodiment of the invention.
Figure 11:
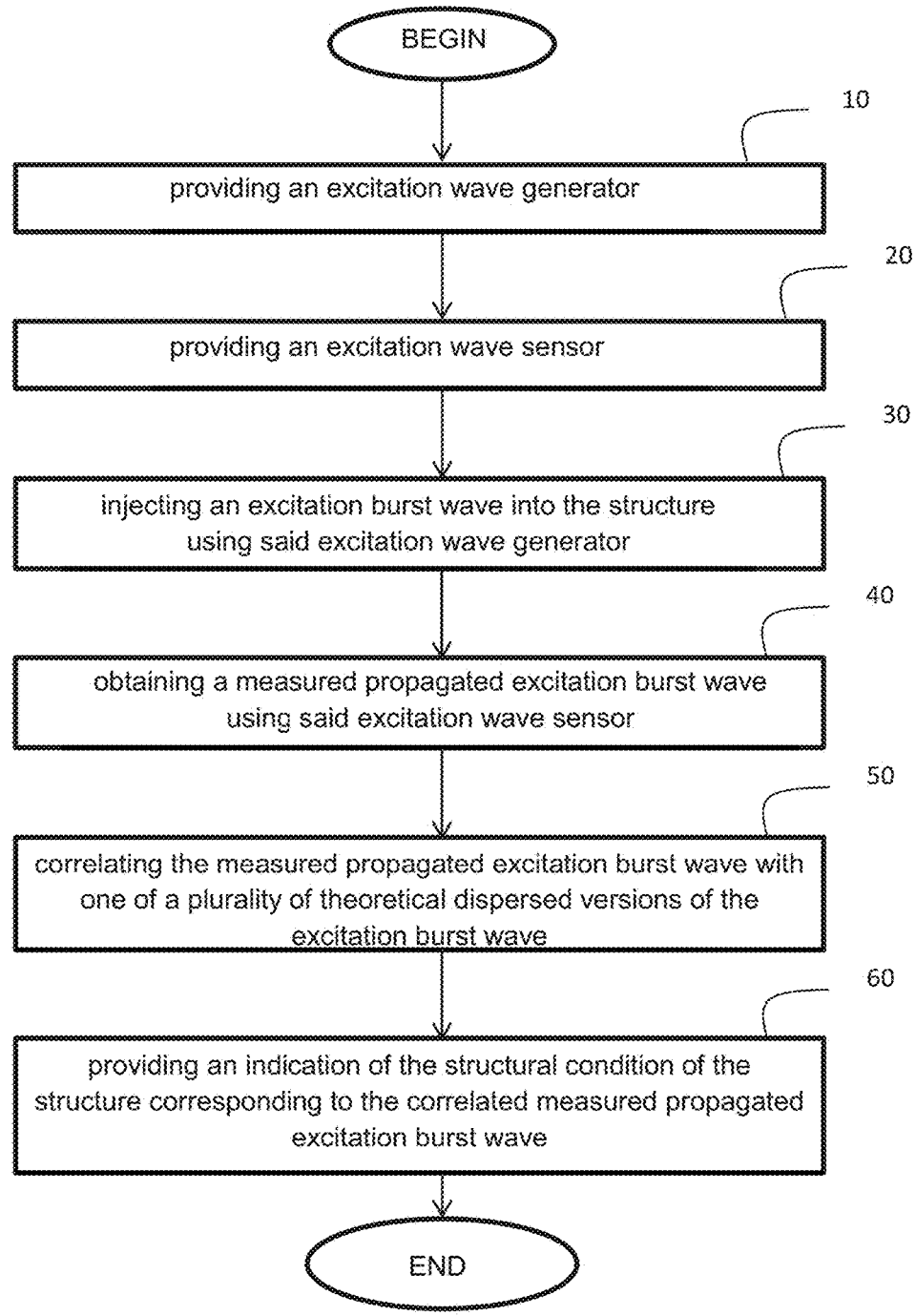
FIG. 11 is a block diagram illustrating a method for providing a structural condition of a structure, according to one embodiment of the invention.

Referring to FIG. 2A, there is shown a plate 100 on which an excitation wave generator 102 and an excitation wave sensor 104 are mounted, according to processing steps 10, 20 of the method which is illustrated on FIG. 11.

In one embodiment, the excitation wave generator 102 and the excitation wave sensor 104 are embedded into the structure 100 for enabling Structural Health Monitoring (SHM).

In another embodiment, the excitation wave generator 102 and the excitation wave sensor 104 may be embedded in a handheld device (not shown) removably mountable with the structure 100 for enabling Non-Destructive Testing (NDT), as it should become apparent below.

Figure 7:
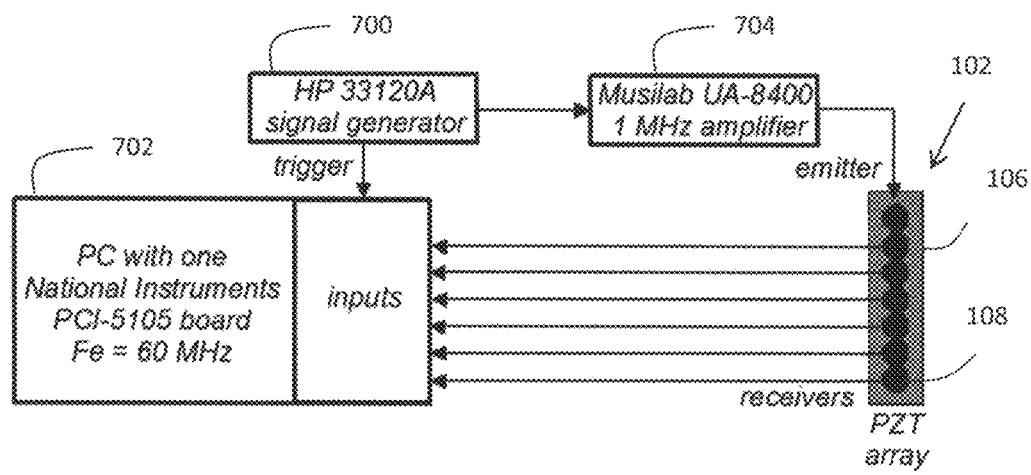
FIG. 7 shows a portion of an apparatus for providing a structural condition of a structure according to another embodiment of the invention.

In one embodiment, as better shown in FIGS. 7 and 2, the excitation wave generator 102 comprises an array 106 of piezoceramic (PZT) actuators 108 mounted on the plate 100 while the excitation wave sensor 104 comprises an array of PZT sensors mounted on the plate, remotely from the piezoceramic actuators 108.

In one embodiment, a piezoceramic element may be used for generating and sensing the appropriate wave, as more detailed below.

Referring now to FIG. 11, according to processing step 30, an excitation burst wave is injected into the structure 100 using the excitation wave generator 102. In one embodiment, the excitation burst wave comprises a high frequency excitation burst wave, ranging for a non-limitative example, from 100 kHz to 2 MHz, but it should be understood that other excitation waves such as audible or ultrasonic waves may be envisaged for a given application.

According to processing step 40, a measured propagated excitation burst wave is obtained using the excitation wave sensor 104.

More precisely, in one embodiment, one or several bursts are injected into a structure 100 by a piezoceramic (PZT) actuator 108 and measurement is conducted by a compact array of PZT sensors, located remotely from the damage 110. The skilled addressee will appreciate that a single burst may be used. However, for a given application, it may be envisaged to use a plurality of bursts.

As it will be detailed below with reference to FIGS. 5A to 6C, the processing steps of injecting and obtaining may be performed according to a pulse-echo configuration in one embodiment, or according to a pitch and catch configuration in another embodiment.

According to processing step 50, the measured propagated excitation burst wave is correlated with one of a plurality of theoretical dispersed versions of the excitation burst wave, as detailed below.

Figure 12:
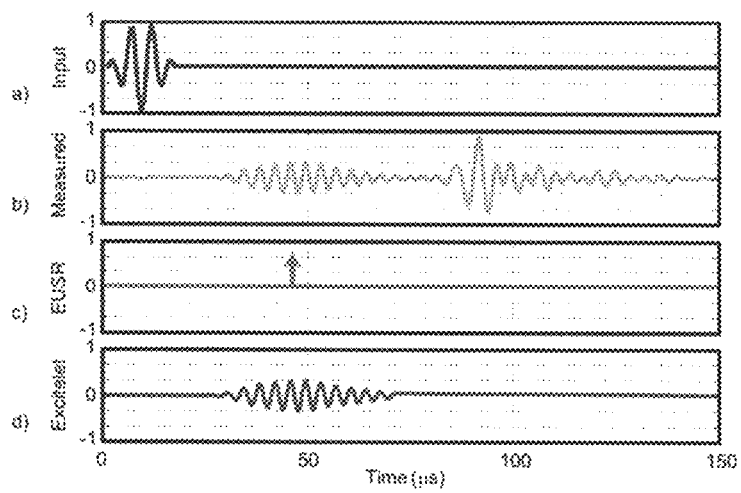
FIG. 12 illustrates a correlation principle of the method and shows an example of a theoretical dispersed version of an excitation burst according to one embodiment of the invention.

FIG. 12(a) shows an exemplary excitation burst wave according to one embodiment while 12(d) shows one theoretical dispersed version of the excitation burst wave, according to the excitelet technique. The skilled addressee will nevertheless appreciate that various other arrangements may be considered.

In one embodiment, the plurality of theoretical dispersed versions of the excitation burst wave is computed based on a theoretical representation of the structure before the processing step 50 of correlating is performed. In a further embodiment, this plurality of theoretical dispersed versions of the excitation burst wave may be stored in a database, as detailed below.

In another embodiment, the plurality of theoretical dispersed versions of the excitation burst wave may be obtained with measurements performed on a reference structure. In this case, before injecting the excitation burst wave into the structure under analysis, a reference structure is first provided. Then, the excitation burst wave is injected into the reference structure using the excitation wave generator. A reference measured propagated excitation burst wave is obtained using the excitation wave sensor. The plurality of theoretical dispersed versions of the excitation burst wave is then computed based on the reference measured propagated excitation burst wave. In one embodiment, this plurality of theoretical dispersed versions of the excitation burst wave may be stored in a database prior to inspecting the structure under analysis, as it should be apparent to the skilled addressee. This may be particularly advantageous for improving the process of Structural Health Monitoring (SHM).

In one embodiment, a matching pursuit algorithm may be implemented with a dictionary of atoms obtained from various dispersed versions of the excitation, wherein the parameters of each atom are the propagation distance and the mode. Therefore, for a selected point in the scan area and a given mode, the measured signal is correlated with a given atom value for each propagation path in the array configuration.

In a further embodiment, a round-robin technique may be used to add the contributions of all these correlation values for each point in the scan area for imaging.

According to processing step 60, an indication of the structural condition of the structure corresponding to the correlated measured propagated excitation burst wave is provided.

In one embodiment, the indication may be the presence or absence of a damage in the structure under analysis. In another embodiment, the indication may be a precise localization of a given defect, as it will become apparent below to the person skilled in the art to which the invention pertains.

In one embodiment, the indication of the structural condition of the structure comprises an image of the structure which may be displayed on a display unit.

Figure 3A:
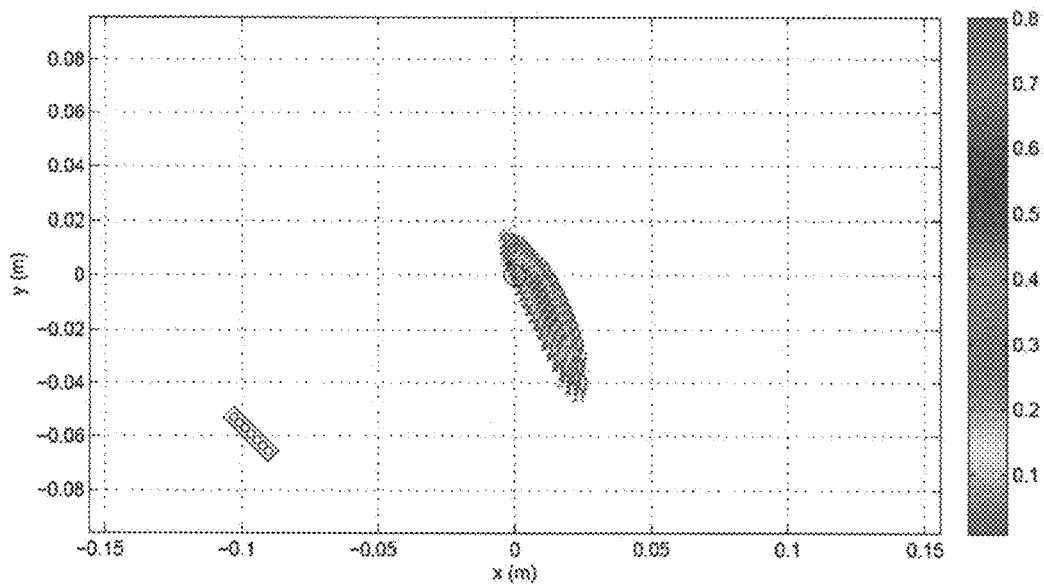
FIGS. 3A and 3B show simulation imaging results for an ideal reflector located at (0,0), with 4.5 cycles at 450 kHz.
Figure 3B:
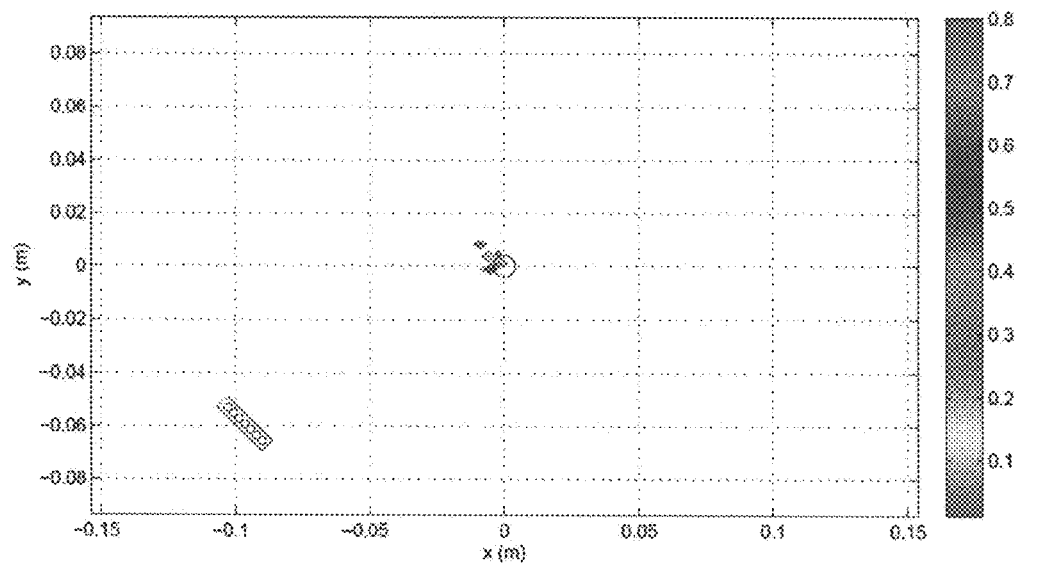

In another embodiment, the indication of the structural condition of the structure comprises an image comprising structural differences between the structure and the reference structure, as shown in FIG. 3B. As it will be detailed thereinafter, in FIG. 3B, the indication shows the location and the size of the defect.

In a further embodiment, the indication may be information related to whether the structure comprises at least one defect or not.

In still a further embodiment, instead of using the phase velocity of the structure for determining the location of an anomaly, the precise propagation distance between the wave generator and the wave sensor and the mode may be used to determine a structural property of the structure. For example, in one embodiment, a phase velocity of the structure may be determined, as it will become apparent to the skilled addressee upon reading the description below.

As previously mentioned, in one embodiment, a portion of the method is similar to the known chirplet-based decomposition approach typically used within the matching pursuit algorithm, except that the analysis atoms are built from theoretical predictions of the excitation signal dispersed by the propagation into the structure, as explained thereinafter.

Indeed, as for many damage detection strategies based on guided wave propagation, in one embodiment, the method uses a burst excitation signal $e_m(t)$ generated by a piezoceramic m in a plate structure and a signal $u_n(t)$ measured by a piezoceramic n.

Figure 1:
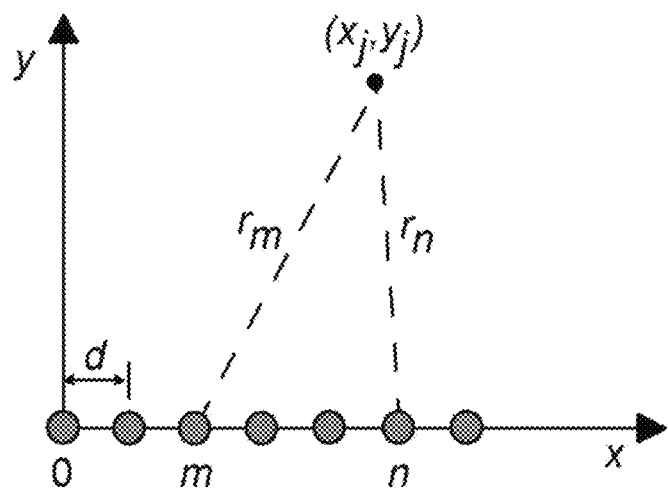
FIG. 1 is a graph illustrating the geometry of a transducer array and a scanning area over a plate, according to one embodiment of the invention.

In one embodiment, a piezoceramic array where the elements are used as both emitters and receivers may be used, as shown in FIG. 1. After generation by an emitter m, the burst propagates into the structure, and is possibly reflected at a target point $(x_i, y_i)$ back to a receiver n. The cylindrical propagation of a given guided wave mode into the plate structure may be simplified to the propagation function $p_{mn}^{mode}(x_j, y_j, c_p^{mode}(\omega), \omega)$ used to relate the stress excitation signal at emitter m to a strain measured at the receiver n:

$$p_{mn}^{mode}(x_j, y_j, c_p^{mode}(\omega), \omega) = F_p(\alpha, \omega) H(x_j, y_j, c_p^{mode}(\omega), \omega) \quad (1)$$

where $$H^m(x_j, y_j, c_p^{mode}(\omega), \omega) = (H_1^{(2)}(k_m(\omega) r_m(x_j, y_j))) (H_1^{(2)}(k_m(\omega) r_n(x_j, y_j))) \quad (2)$$

where $\omega$ denotes the angular frequency, $k_m(\omega) = \omega/c_p^{mode}(\omega)$ the wavenumber associated with mode m, $H_1^{(2)}$ is the complex Hankel function of first order and second kind, $F_p(\alpha,\omega)$ stands for the frequency dependence of the amplitude of the generated Lamb wave due to the piezoceramic (with diameter a) coupling with host structure, and $r_m(xj, yj)$ and $r_n(xj, yj)$ represent the propagation distance defined by:

$$r_m(x_j, y_j) = \sqrt{(x_j-x_m)^2+(y_j-y_m)^2}, \qquad (3)$$

$$r_n(x_j, y_j) = \sqrt{(x_j-x_n)^2+(y_j-y_n)^2}. \qquad (4)$$

Considering far-field radiation such that $|k_m(\omega) r_m(x_j,y_j)| \gg 1$, Eq. 2 can be approximated for computational efficiency by:

$$H^m(x_j, y_j, c_p^{mode}(\omega), \omega) = \qquad (5)$$
$$A \frac{2c_p^{mode}(\omega)}{\pi\omega} \sqrt{\frac{1}{r_m(x_j, y_j)}} \sqrt{\frac{1}{r_n(x_j, y_j)}} e^{-i\left((r_m(x_j,y_j)+r_n(x_j,y_j))k_m(\omega)-\frac{\pi}{2}\right)},$$

The formulation for $F_p(\alpha,\omega)$ can be found for various piezoceramic geometries such as rectangular piezoceramics. Two formulations are presented herein as non-limitative examples, i.e. point excitation and circular excitation:

$$F_p(a, \omega) = 1 \text{ for point excitation} \qquad (6)$$

$$F_p(a, \omega) = aJ_1(k_m(\omega)a)\frac{N_m(k_m(\omega))}{D'_m(k_m(\omega))} \text{ for circular} \qquad (7)$$

piezoceramic excitation in isotropic structures where a is the radius of the piezoceramic, $J_1$ is the Bessel function of the first kind and order 1, ' denotes the derivative with respect to $k_m(\omega)$, and $N_m$ and $D_m$ are defined for symmetric modes as:

$$N_m^s(k_m)=k_m q(k_m^2+q^2)\cos(ph)\cos(qh) \qquad (8)$$

$$D_m^s(k_m)=(k_m^2-q^2)^2 \cos(ph)\sin(qh)+4k_m^2 pq \cos(ph)\sin(qh) \qquad (11)$$

and for antisymmetric modes as:

$$N_m^a(k_m)=k_m q(k_m^2+q^2)\sin(ph)\sin(qh) \qquad (10)$$

$$D_m^a(k_m)=(k_m^2-q^2)^2 \sin(ph)\cos(qh)+4k_m^2 pq \cos(ph)\sin(qh) \qquad (11)$$

where the dependency of $k_m$ on $\omega$ has been dropped for clarity. p and q are defined as:

$$p^2 = \frac{\omega^2}{c_P^2} - k_m^2, \qquad (12)$$

$$q^2 = \frac{\omega^2}{c_S^2} - k_m^2$$

where $c_p$ is the pressure wave velocity and $c_s$ is the shear wave velocity.

Then, using the inverse Fourier transform, the theoretical shape of the strain generated by the burst possibly reflected at target point $(x_i, y_j)$ and propagated back to element n may be expressed by:

$$s_{mn}^{mode}(x_j,y_j,t,c_p^{mode}(\omega))=\int_{-\infty}^{\infty}E_m(\omega)p_{mm}^{mode}(x_j,y_j,c_p^{mode}(\omega),\omega) e^{i\omega t}d\omega, \qquad (13)$$

where $E_m(\omega)$ is the Fourier transform of the excitation burst $e_m(t)$.

In one embodiment of the proposed method, a correlation coefficient is then obtained for each coordinate $(x_j, y_j)$ on the surface. For a given pair of emitter and receiver, the correlation coefficient between the measured signal $u_n(t)$ at receiver n and the simulated propagated burst $s_{mm}^{mode}(x_j, y_j, t, c_p^{mode}(\omega))$ may be expressed as:

$$c_{mn}^{mode}(x_j, y_j, c_p^{mode}(\omega)) = \frac{\int u_n(t)s_{mn}^{mode}(x_j, y_j, t, c_p^{mode}(\omega))dt}{|u_n(t)||s_{mn}^{mode}(x_j, y_j, t, c_p^{mode}(\omega))|}. \qquad (14)$$

This correlation coefficient indicates how well the measured signal $u_n(t)$ at a receiver n correlates with a mode excited at an emitter m by a burst $e_m(t)$ and propagated over a distance $r_m$, and then over a distance $r_n$.

As mentioned above, in one embodiment, Eq. (14) may be used for providing an image of the structure. In this case, the phase velocity of the structure is assumed to be known.

In another embodiment, Eq. (14) is used for determining the phase velocity of the structure and then some of the mechanical properties thereof such as the Young's modulus and the Poisson's ratio. In this case, $(x_j, y_j)$, i.e. the propagation distance, is known.

As it should be understood by the skilled addressee, the excitelet approach presented herein may be implemented into an imaging strategy to map the possible reflectors within a given scanned area. As mentioned above, the imaging approach uses an array of actuators and sensors to generate and measure guided wave propagation into the structure.

In one embodiment, as illustrated in FIG. 7, the selected array is a linear array 106 with seven regularly spaced circular elements 108. Although the imaging method may be implemented with arrays of more complicated geometries, such as two-dimensional rectangular or circular patterns, and sparse array of transducers as it will be described thereinafter, the linear array may be selected to provide a simple common ground in the relative performance evaluation using two imaging techniques.

In one embodiment, the imaging method is implemented with a round-robin procedure to localize defects in the structure. The M elements of the array are fired in a round-robin fashion and the measurement is conducted using the N other elements (N=M−1). A sampled burst excitation signal $e_m(t)$ is generated at the emitting element and spatial representation of the signal reflected by a target located at $(x_j, y_j)$ is obtained using the signals measured at the receivers.

In this embodiment, an image of the reflectors is obtained by combining the correlation coefficients obtained for all the pairs of emitter-receiver and scanning all the points within an area of the structure.

Moreover, multiple mode correlation may be used to increase the resolution of the image by multiplying the results for each mode, as it will become apparent to the skilled addressee:

$$E_{excitelet}(x_j, y_j) = \prod_{mode}^{A_0,S_0,\ldots} \sum_{m=1}^{M} \sum_{n\neq m} c_{mn}^{mode}(x_j, y_j). \qquad (15)$$

Another multiple mode correlation relying on adding the results for each mode may also be implemented:

$$E_{excitelet}(x_j, y_j) = \sum_{mode}^{A_0, S_0, \ldots} \sum_{m=1}^{M} \sum_{n \neq m} c_{mn}^{mode}(x_j, y_j). \quad (16)$$

The skilled addressee will appreciate that modes $A_0$ and $S_0$ may be used to demonstrate the interest of using multiple mode correlation but it should be understood that it may be extended to other modes.

Thereinafter, the proposed method will be compared with the EUSR technique. The EUSR technique is an implementation of a phased-array technique, which also uses a round-robin procedure, to image defects located in the far-field of the array, although defects located in the near field may also be imaged using triangulation principles. In its simplest implementation, the approach uses delays applied to the measurement signals to steer the beam in a given direction. The spatial representation of the signal possibly reflected by a target located at $(x_j, y_j)$ is given by extracting and adding time domain components of the signals $u_n(t)$ received at each of the N receivers:

$$s(x_j, y_j) = \qquad \text{Eq. (17)}$$
$$\sum_{m=1}^{M} \sum_{n \neq m} \sqrt{r_m(x_j, y_j)} \sqrt{r_n(x_j, y_j)} u_n(\Delta\phi_m + \Delta\phi_n + \Delta\phi_{burst}),$$

where $\sqrt{r_m(x_j,y_j)}$ and $\sqrt{r_n(x_j,y_j)}$ are used to compensate for synthetic cylindrical propagation in the plate, $\Delta\phi_{burst}$ is a time delay corresponding to half of the excitation burst width and:

$$\Delta\phi_m = \frac{r_m(x_j, y_j)}{c_g} \qquad \text{Eq. (18)}$$

and $$\Delta\phi_n = \frac{r_n(x_j, y_j)}{c_g},$$

and $c_g$ is the group velocity at the center frequency of the burst propagating in the plate. No dissipation is assumed and dispersion is considered to be minimized by a proper choice of the excitation frequency. The mapping of the energy of the received signal as a function of the location is then given by:

$$E_{EUSR}(x_j, y_j) = |s(x_j, y_j)|^2. \qquad \text{Eq. (19)}$$

A simulation has been conducted where the propagation of a given Lamb mode has been simulated analytically assuming cylindrical propagation. The goal of the simulation is to evaluate how an approach exploiting the dispersion of guided waves compares with an approach based on the use of the group velocity using ToF to localize a reflector.

The simulation was performed for a 1.5 mm thick aluminum plate 100, such as presented in FIG. 2A. The array 102 of seven elements represented on the left in FIG. 2A is used for the simulation. A perfect reflector 110, with reflection coefficient equal to 1, is simulated and located at coordinates (0,0) on the plate 100. The properties used for the simulation are presented in FIG. 2B (Table 1), except for the hole which is not considered in the simulation. For the simulation with the EUSR approach, $c_g$=2984 m/s.

FIG. 3 shows the imaging results obtained using the proposed excitelet approach with Eq. (15) in FIG. 3B and using EUSR with Eq. (19) in FIG. 3A. For the purpose of better illustrating the effect of considering the dispersion in the imaging approach, the propagation of the $A_0$ mode is simulated at 450 kHz, using 4.5 cycles burst.

The results presented in FIG. 3A indicate that the EUSR approach tends to provide a rather wide and curved area around the simulated reflector. Moreover, the localization of the reflector is biased by more than 1 cm. On the other hand, the results presented in FIG. 3B show that the excitelet approach has the potential to localize the reflector 110 with a higher resolution, which is of great advantage.

Experimental results as well as an experimental setup will now be described in more details according to one embodiment.

In the experiment, the imaging method is implemented for the detection of a notch having a length of 2 mm and a width of 0.8 mm from the side of a hole in an aluminum plate 100 with the properties presented in FIG. 2B (Table 1). Two piezoelectric arrays are bonded to the plate following the schematics presented in FIG. 2A, but only the left one is used in this experiment.

In this embodiment, the arrays are manufactured in a bulk piezoceramic (PZT) using laser micro-machining to cut the upper electrode with circular patterns. As mentioned before, the seven elements of the array are fired in a round robin fashion and the measurement is conducted using the six other elements. FIG. 7 presents the connections for one of the round-robin iterations, according to one embodiment.

A signal generator 700, Hewlett-Packard™ 33120A as an example, with a sampling frequency of 15 MHz is used to generate the burst. An acquisition board 702, National Instruments™ PCI-5105 as an example, is used to record signals with a sampling frequency of 60 MHz from the piezoelectric elements. A Musilab™ UA-8400 high voltage and large bandwidth (1 MHz) amplifier 704 is used to amplify the excitation signals generated by the board to approximately 60 Vpk. Bursts of 2.5 cycles are used to excite Lamb modes $A_0$ and $S_0$ at frequencies such that the diameter of the elements corresponds to half of a wavelength for a given mode, which leads to a frequency of 300 kHz for the $A_0$ mode and a frequency of 850 kHz for the $S_0$ mode. Another intermediate frequency of 500 kHz is also used in this experiment to better illustrate the interest of multiple mode correlation, as it will become apparent to the skilled addressee. The excitelet approach is implemented on the scatter signal, i.e. the difference between the signal measured on the plate with a hole only and the signal measured on the plate with a hole and a notch.

The experimental results are presented in FIGS. 8 through 10, where the amplitude has been normalized to better compare the images. Scatter imaging results are presented, obtained by subtracting the healthy time signal (obtained with a reference plate without defect) from the damaged time signal (obtained with a plate having a notch therein).

Figure 8A:
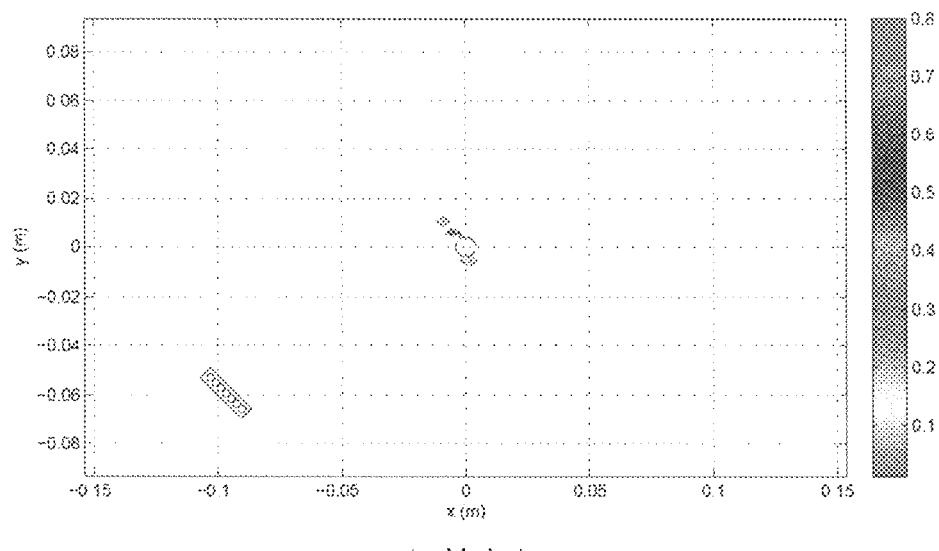
FIGS. 8A and 8B are graphical representations showing experimental imaging results using the scatter signal with the excitelet approach at 300 kHz according to one embodiment of the invention.
Figure 8B:
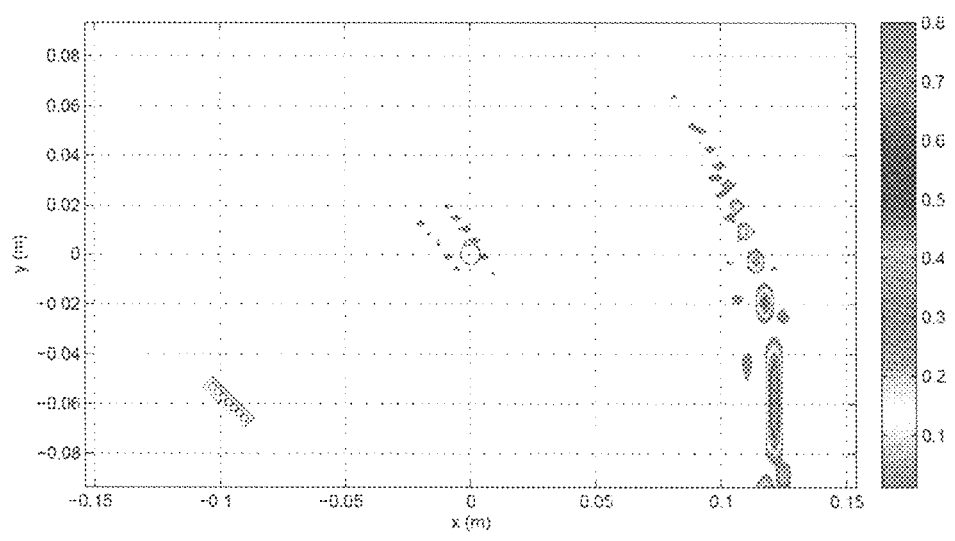

The results shown in FIGS. 8A and 8B illustrate that the excitelet technique localizes correctly the notch for both $A_0$ and $S_0$ modes at 300 kHz. As predicted, at this frequency, where the $A_0$ mode is dominant (the $S_0$ mode is not generated, since its wavelength corresponds to the size of the actuator), the localization of the notch is better performed with the $A_0$ mode.

Figure 9A:
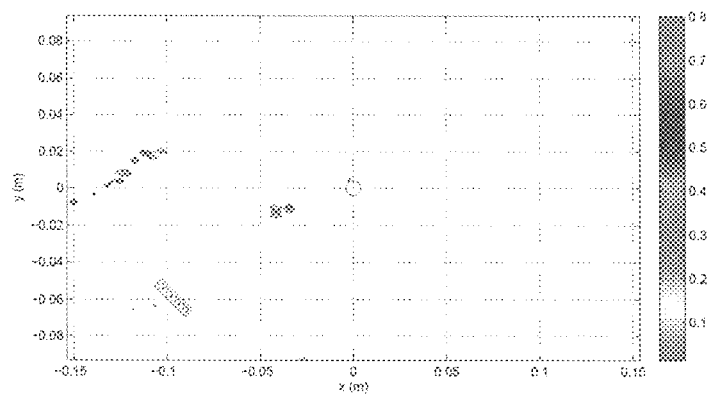
FIGS. 9A and 9B are graphical representations showing experimental imaging results using the scatter signal with the excitelet approach at 850 kHz according to another embodiment of the invention.
Figure 9B:
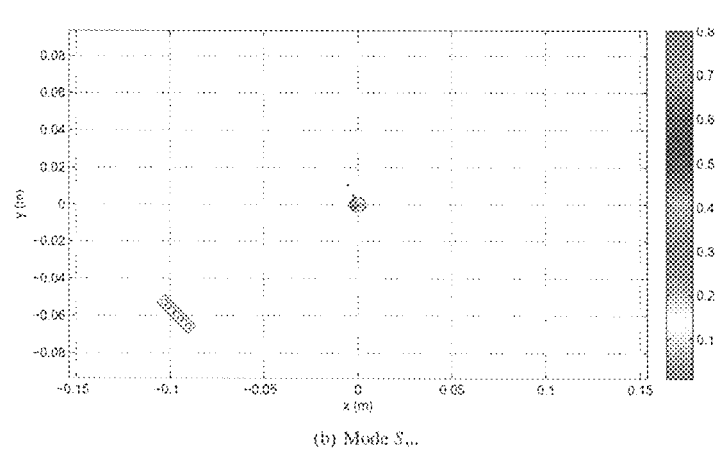

The results shown in FIGS. 9A and 9B illustrate that the excitelet technique localizes correctly the notch for both $A_0$ and $S_0$ modes at 850 kHz. As predicted, at this frequency, where the $S_0$ mode is dominant (the $A_0$ mode is not generated, since its wavelength corresponds to the size of the actuator), the localization of the notch is better performed with the $S_0$ mode.

Figure 10A:
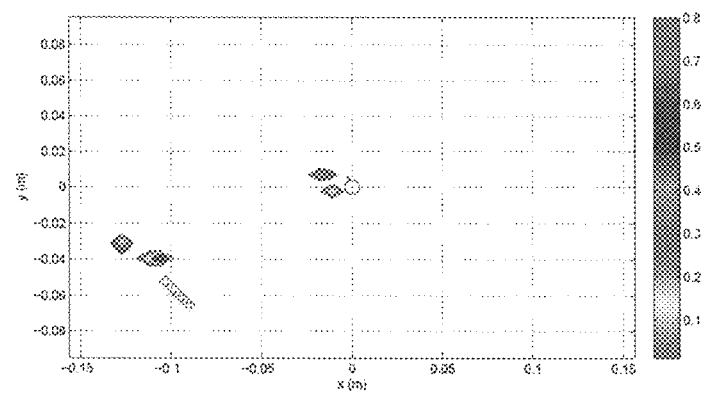
FIGS. 10A to 10C are graphical representations showing experimental imaging results using multiple mode correlation with the excitelet approach using modes $A_0$ and $S_0$ for damage detection at 500 kHz according to another embodiment of the invention.
Figure 10B:
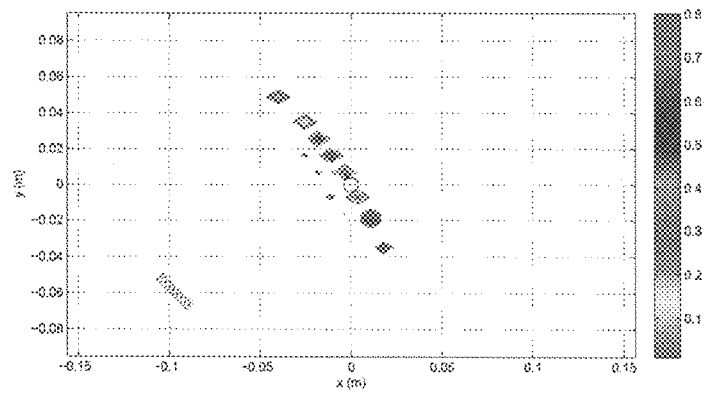
Figure 10C:
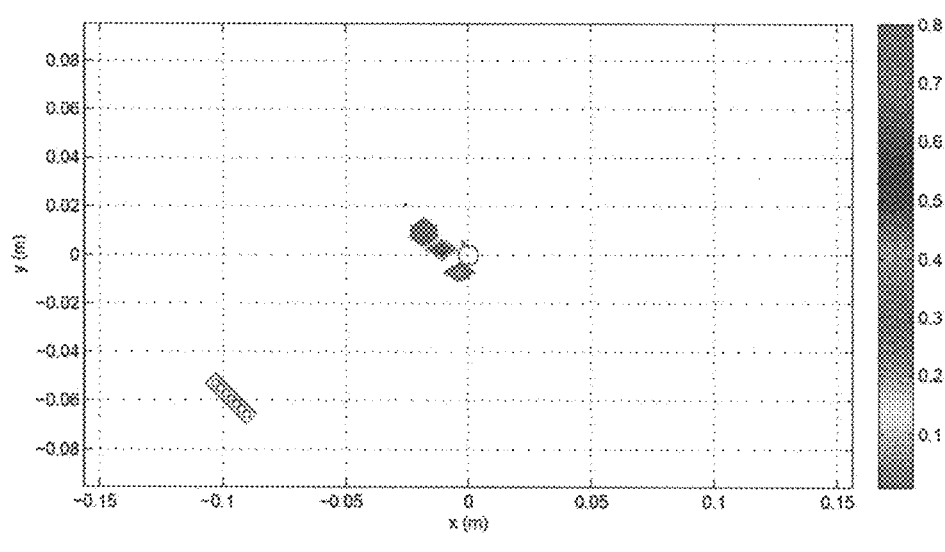

The skilled addressee will appreciate that the results shown in FIGS. 10A through 10C show the interest of using multiple mode correlation. A frequency of 500 kHz has been selected for this case, where both $A_0$ and $S_0$ modes are excited by the actuator. The localization of the notch is presented in FIG. 10A using the $A_0$ mode and in FIG. 10B using the $S_0$ mode. It can be observed that considering both modes individually, the localization is contaminated by the other mode also propagating. FIG. 10C shows the localization obtained by implementing the multiple mode correlation, as expressed in Eq. (15). This result tends to indicate that significant improvement may be obtained in the imaging using the excitelet approach when multiple modes are propagating.

The skilled addressee will appreciate that the experiment demonstrates that better resolution may be obtained for the localization of the reflection point (the defect in the plate) with the excitelet approach, when compared with a group velocity-based, or ToF approach.

The simulation results were validated experimentally using a 1.5 mm thick aluminium plate with a notch in the periphery of a hole. Bonded PZTs were used for both actuation and sensing of 2.5 cycles bursts at 300 kHz, 500 kHz and 850 kHz. Results were presented for single mode and multiple mode correlation. Single mode correlation demonstrated high resolution imaging while multiple mode correlation allowed proper localization for multiple modes propagating in the structure. These results tend to indicated that significant improvement of imaging quality is demonstrated with the excitelet approach when compared with classical imaging techniques.

Throughout the present description, the method has been described using PZT elements bonded on the surface of a plate as actuators and sensors but it should be understood that various other actuators and sensors as well as various others configurations may be used, as it should become apparent below.

For example, the PZT elements may be embedded in the structure itself. This may be of great advantage for implementing a Structural Health Monitoring (SHM). The PZT elements may also be mounted in a handheld device for enabling Non-Destructive Testing (NDT), as previously mentioned.

Piezoelectric polymers (PVDFs) as well as conventional ultrasonic transducer such as ultrasonic wedge transducers may also be used. The skilled addressee will indeed understand that any actuator adapted for generating a controlled wave may be considered. For example a thermal wave generated with a laser may be convenient for implementing the method. The skilled addressee will also appreciate that the PZT elements may be used as both an actuator and a sensor, as mentioned above.

Figure 4:
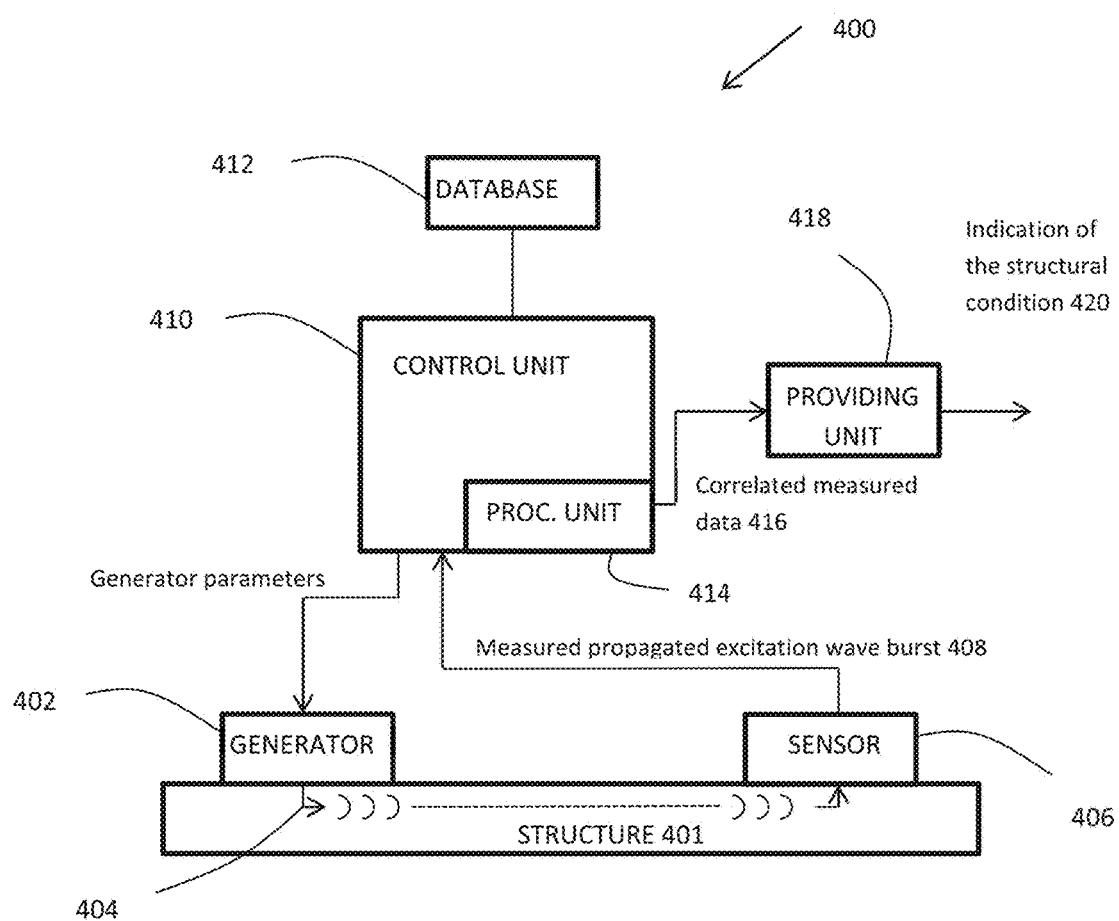
FIG. 4 is a schematic illustration of an apparatus for providing a structural condition of a structure, according to one embodiment of the invention.

Referring to FIG. 4, an apparatus 400 for providing a structural condition of a structure will now be described.

The apparatus 400 comprises an excitation wave generator 402 operatively mountable with the structure 401 for injecting an excitation burst wave 404 into the structure 401 and an excitation wave sensor 406 operatively mountable with the structure 401 for obtaining a measured propagated excitation wave burst 408.

The apparatus 400 comprises a control unit 410 operatively connected to the excitation wave generator 402 and to the excitation wave sensor 406. The control unit 410 is further operatively connectable to a database 412 comprising a plurality of theoretical dispersed versions of the excitation burst wave, as detailed therein.

The control unit 400 comprises a processing unit 414 adapted for correlating the measured propagated excitation wave burst 408 with one of the plurality of theoretical dispersed versions of the excitation burst wave to provide correlated measured data 416, as detailed above.

The apparatus 400 comprises a structural condition providing unit 418 operatively connected to the control unit 410 for providing an indication of the structural condition of the structure 420 corresponding to the correlated measured data 416. The structural condition providing unit 418 may comprise a display unit although other arrangements may be considered.

As previously mentioned, in one embodiment, each of the excitation wave generator 402 and the excitation wave sensor 406 may be embedded in the structure 401 while, in another embodiment, the excitation wave generator 402 and the excitation wave sensor 406 may be embedded in a handheld device removably mountable with the structure 401.

Figure 5A:
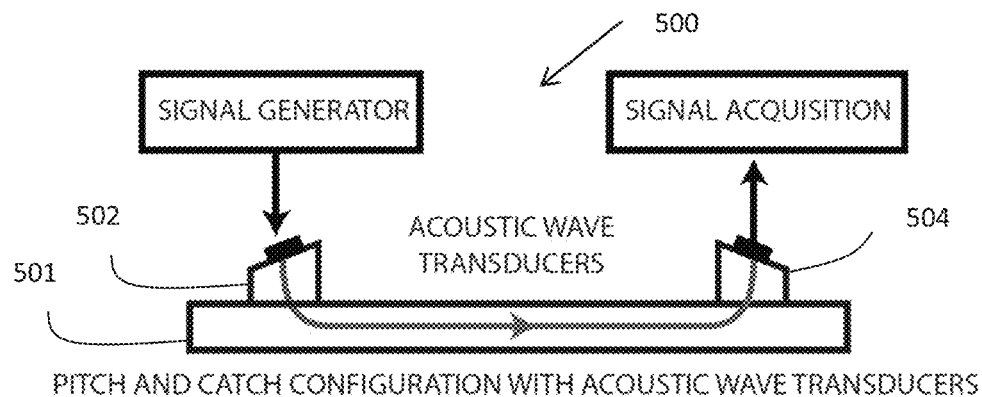
FIGS. 5A to 5C shows various embodiments of an apparatus for providing a structural condition of a structure wherein the excitation wave generator and the excitation wave sensor are embedded in a handheld device removably mountable with the structure.
Figure 5B:
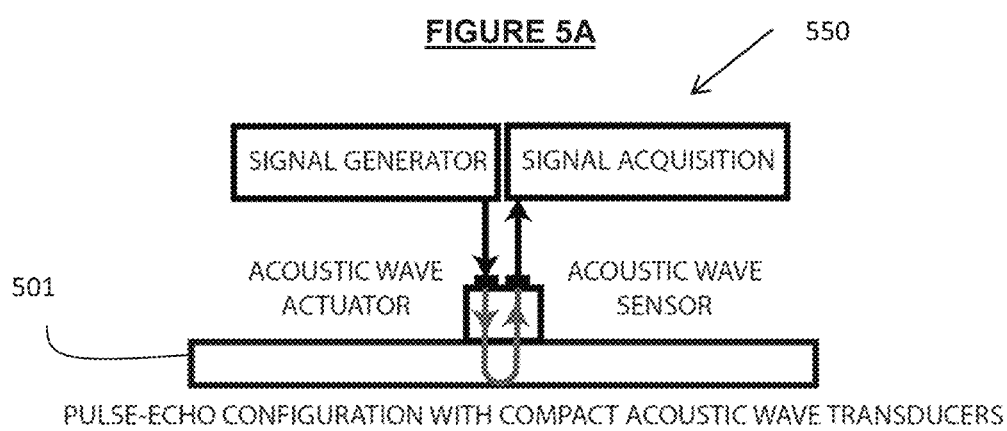
Figure 5C:
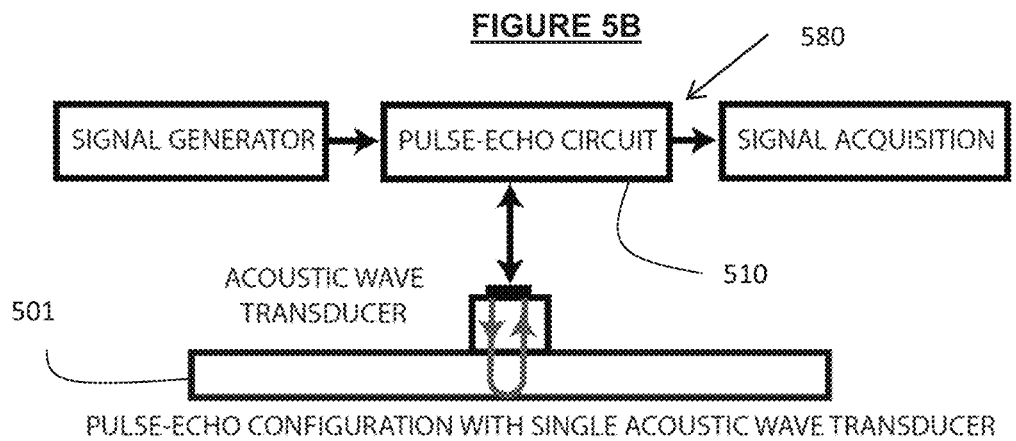

FIGS. 5A to 5C illustrates portable devices 500, 550 and 580 used for Non-Destructive Testing (NDT). The portable device 500, 550, 580 may be removably attached to the structure 501 under inspection.

FIG. 5A illustrates a pitch and catch configuration using two distant transducers 502, 504 while FIGS. 5B and 5C illustrate two distinct pulse-echo-configurations, the second one using a pulse-echo circuit 510.

Figure 6A:
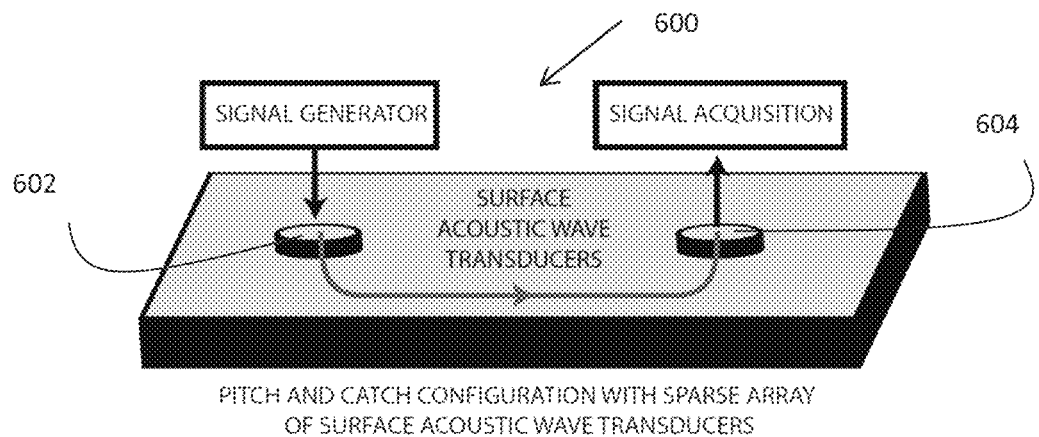
FIGS. 6A to 6C show various embodiments of an apparatus for providing a structural condition of a structure wherein the excitation wave generator and the excitation wave sensor are embedded into the structure.
Figure 6B:
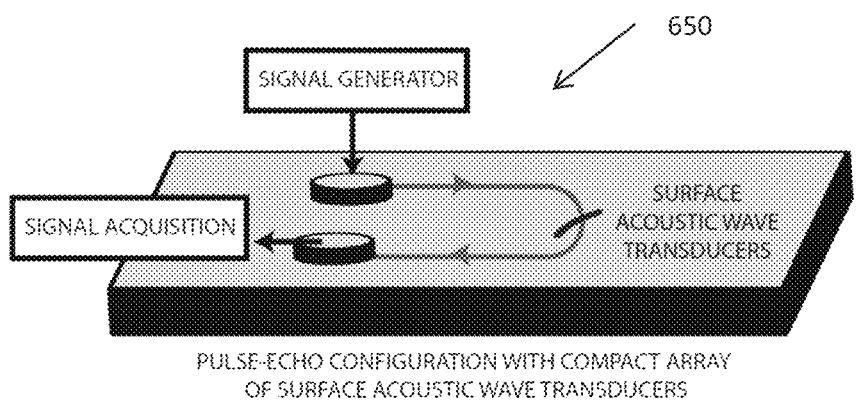
Figure 6C:
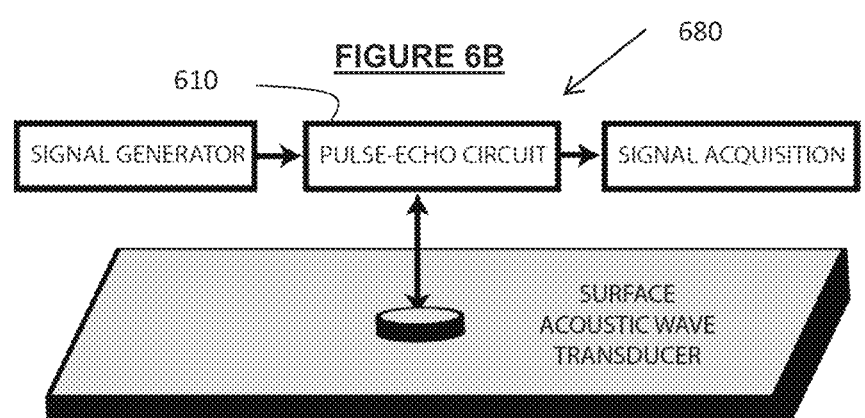

FIGS. 6A to 6C illustrate integrated devices 600, 650 and 680 used for Non-Destructive Testing (NDT). As illustrated, the excitation wave generator 602 and the excitation wave sensor 604 are permanently embedded in the structure.

FIG. 6A illustrates a pitch and catch configuration using two distant transducers 602, 604 while FIGS. 6B and 6C illustrate two distinct pulse-echo-configurations, the second one using a pulse-echo circuit 610.

As previously mentioned, in one embodiment, the excitation wave generator and the excitation wave sensor are embedded in a single transducer adapted for injecting the excitation burst wave into the structure and obtaining the measured propagated excitation burst wave.

As previously mentioned, in a further embodiment, the transducer comprises an array of elements operable according to a round-robin technique.

In one embodiment, the excitation wave generator and the excitation wave sensor are combined in a sparse array of transducers. Indeed, it has been validated that results obtained using the excitelet algorithm are valid in both sparse and compact configurations. However, further experiments have shown that the localization using the compact array may be more subject to false calls than using the sparse array. For instance, in the experiment, at 350 kHz, A0 mode imaging leads to false damage estimation using the compact array while in the sparse configuration, both modes may be used and thus the multimodal reconstruction points out two real damages.

Moreover, it has also been shown that when used with the compact array, the algorithm may suffer from sensitivity to the measurement noise. Indeed, the results obtained at 550 kHz show that the near-field imaging (i.e. for observation distance below 10 cm) is impaired by noise issued from subtraction of the measured pristine and damaged signals in the round-robin process. In that case, only one of the two damages is visible, while in the case of the sparse array of transducers, both damages are clearly visible.

However, in the sparse configuration, the imaging process is limited to the inside of the array and extension to the outside cannot be performed while the compact imaging is only limited in distances of detection by the attenuation of the generated guided waves (above 1 m in the present case). Depending on the inspected geometries and materials, this aspect may be taken into account when designing a SHM system.

Although the above description relates to specific preferred embodiments as presently contemplated by the inventors, it will be understood that the invention in its broad aspect is not limited to this specific embodiment and includes mechanical and functional equivalents of the elements described herein.

What is claimed is:

1. An apparatus for providing a structural condition of a structure, the apparatus comprising:

an excitation wave generator operatively mountable with the structure for injecting an excitation burst wave into the structure at a given emission location, the excitation burst wave propagating in the structure;

an excitation wave sensor operatively mountable with the structure at a given reception location for obtaining a measured propagated excitation burst wave;

a control unit operatively connected to the excitation wave generator and to the excitation wave sensor, the control unit being further operatively connectable to a database comprising a plurality of theoretical dispersed versions of the excitation burst wave, each one of the plurality of theoretical dispersed versions of the excitation burst wave corresponding to a reflection of the excitation burst wave at a respective one of a plurality of target points within the structure for a respective emission location for the excitation wave generator and a respective reception location of the excitation wave sensor, the control unit comprising a processing unit adapted for cross-correlating the measured propagated excitation burst wave with the plurality of theoretical dispersed versions of the excitation burst waves to obtain a plurality of cross-correlation coefficients each between the measured propagated excitation burst wave detected at the given reception location and a respective one of the plurality of theoretical dispersed versions of the excitation burst wave; and a structural condition providing unit operatively connected to the control unit for providing an indication of the structural condition of the structure using the obtained plurality of cross-correlation coefficients.

2. The apparatus for providing a structural condition of a structure according to claim 1, wherein the excitation wave generator and the excitation wave sensor are embedded in a handheld device removably mountable with the structure.

3. The apparatus for providing a structural condition of a structure according to claim 1, wherein the excitation wave generator and the excitation wave sensor are embedded in a single transducer adapted for injecting the excitation burst wave into the structure and obtaining the measured propagated excitation burst wave.

4. The apparatus for providing a structural condition of a structure according to claim 1, the apparatus being adapted for determining a structural property of the structure.

5. The apparatus for providing a structural condition of a structure according to claim 4, wherein the structural property of the structure comprises a phase velocity of the structure.

6. The apparatus for providing a structural condition of a structure according to claim 1, wherein the plurality of theoretical dispersed versions of the excitation burst wave are computed based on a theoretical representation of the structure.

7. The apparatus for providing a structural condition of a structure according to claim 1, wherein the plurality of theoretical dispersed versions of the excitation burst wave are obtained with measurements performed on a reference structure.

8. The apparatus for providing a structural condition of a structure according to claim 1, wherein the structural condition providing unit is further adapted to generate an image of the structure.

9. The apparatus for providing a structural condition of a structure according to claim 8, wherein the structural condition providing unit is adapted to implement a round-robin procedure to localize defects in the structure.

* * * * *

UNITED STATES PATENT AND TRADEMARK OFFICE
CERTIFICATE OF CORRECTION

PATENT NO. : 9,733,217 B2
APPLICATION NO. : 13/582822
DATED : August 15, 2017
INVENTOR(S) : Masson et al.

It is certified that error appears in the above-identified patent and that said Letters Patent is hereby corrected as shown below:

On the Title Page

Item (73), The correct name of the Assignee should be Socpra Sciences et Génie s.e.c., rather than Scopra Sciences et Génie s.e.c Signed and Sealed this
Twenty-second Day of May, 2018

Andrei Iancu
*Director of the United States Patent and Trademark Office*